(12) United States Patent
Marafko

(10) Patent No.: US 11,975,127 B2
(45) Date of Patent: May 7, 2024

(54) BREAST MILK COLLECTION AND STORAGE CONTAINERS AND SYSTEMS THEREOF

(71) Applicant: Lactation Biocience LLC, Atanta, GA (US)

(72) Inventor: Colin Marafko, Atlanta, GA (US)

(\*) Notice: Subject to any disclaimer, the term of this patent is extended or adjusted under 35 U.S.C. 154(b) by 891 days.

(21) Appl. No.: 17/018,955

(22) Filed: Sep. 11, 2020

(65) Prior Publication Data
US 2021/0077674 A1 Mar. 18, 2021

Related U.S. Application Data
(60) Provisional application No. 62/899,470, filed on Sep. 12, 2019.

(51) Int. Cl.
*A61J 9/00* (2006.01)
*A61M 1/06* (2006.01)
*A61M 39/24* (2006.01)

(52) U.S. Cl.
CPC .............. *A61M 1/064* (2014.02); *A61J 9/005* (2013.01); *A61J 2200/44* (2013.01); *A61J 2200/76* (2013.01); *A61M 2039/2433* (2013.01); *A61M 2205/3606* (2013.01)

(58) Field of Classification Search
CPC ........ A61M 1/06; A61M 1/062; A61M 1/064; A61M 1/066; A61M 39/24; A61J 11/04; A61J 9/08; A61J 9/085; A61J 1/2003; A61J 1/2006; A61J 1/201; A61J 9/005; A61J 9/001; A61J 1/10; A61J 2200/40; A61J 2200/44; A61J 9/06; A61J 9/0661; A61J 1/00; A61J 3/00; A61J 9/00; A23C 9/206; A01N 1/021; A01N 1/0226; A01N 1/0278; A01N 1/0284
See application file for complete search history.

(56) References Cited

U.S. PATENT DOCUMENTS

| | | | |
|---|---|---|---|
| 6,991,121 B1 * | 1/2006 | Kipperman | A61J 9/005 |
| | | | 215/11.1 |
| 2002/0156419 A1 * | 10/2002 | Silver | A61M 1/06 |
| | | | 604/74 |
| 2015/0290081 A1 * | 10/2015 | Kropczynski | A61J 1/2082 |
| | | | 604/244 |
| 2020/0179233 A1 * | 6/2020 | Venti | A61J 9/085 |
| 2020/0330330 A1 * | 10/2020 | Chenvainu | A61J 9/001 |

FOREIGN PATENT DOCUMENTS

CN 205924562 U * 2/2017

\* cited by examiner

*Primary Examiner* — Nathan R Price
*Assistant Examiner* — Anna E Goldberg-Richmeier
(74) *Attorney, Agent, or Firm* — Polsinelli PC

(57) ABSTRACT

A breast milk collection and storage system and methods of use is described. The breast milk collection and storage system may include a milk container operable to hold and store breast milk for an extended period of time. The milk container may include a container wall with an oxygen blocking layer, a light blocking layer, and an inner surface that is non-adherent for lipids and proteins, a container opening surrounded by the container wall, and a foil seal operable to seal the container opening. The milk container may have low oxygen head space and a storage system to enable the rapid cooling of the breast milk.

5 Claims, 15 Drawing Sheets

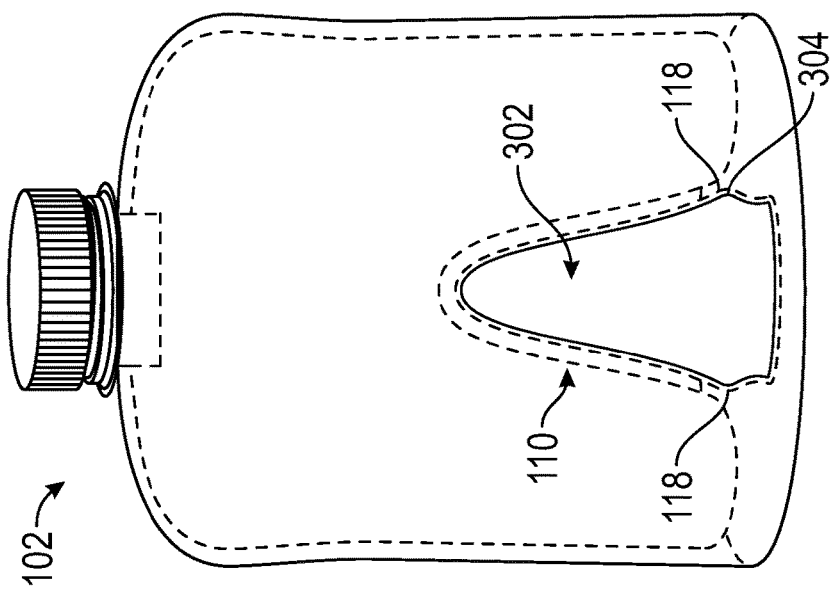
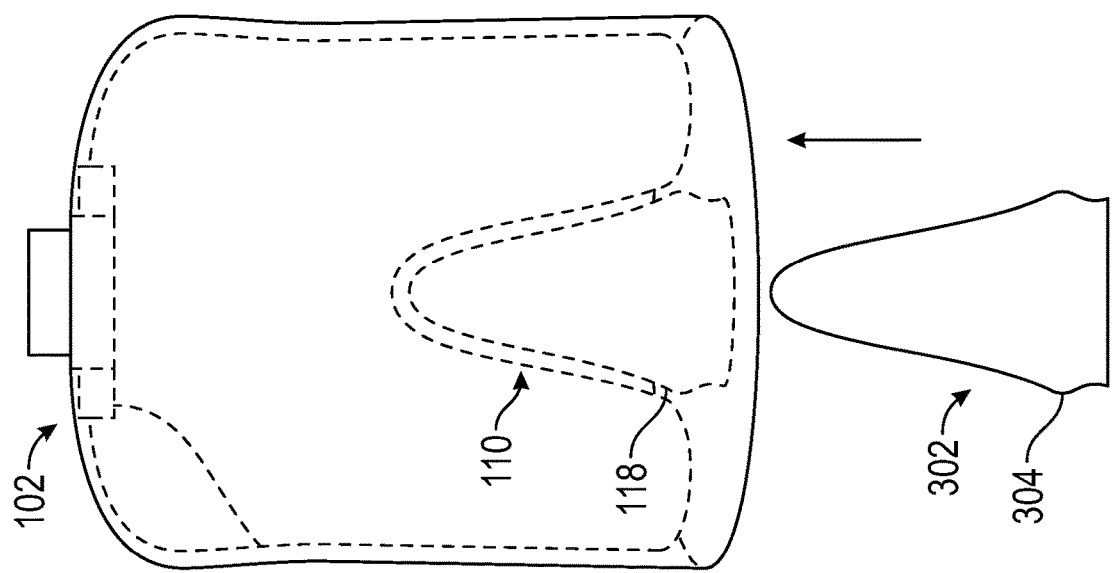

BREAST MILK COLLECTION AND STORAGE CONTAINERS AND SYSTEMS THEREOF

CROSS-REFERENCE TO RELATED APPLICATIONS

This application claims priority under 35 USC § 119(e) to U.S. Patent Application Ser. No. 62/899,470, filed on Sep. 12, 2019, the entire contents of which are hereby incorporated by reference.

FIELD

The present disclosure relates generally to systems and methods to collect and store colostrum, human milk, and/or breast milk. In at least one example, the present disclosure relates to systems and methods to provide light and oxygen protective milk collection and storage with rapid cooling and low lipid binding surfaces.

BACKGROUND

Breast milk is a complex fluid with a composition that changes from day to day and throughout the growth of the infant. Because breast milk is a living mixture, collecting, storing freezing, thawing and warming breast milk can degrade the beneficial properties of this critical source of nutrition. Breast milk constituents can quickly degrade due to oxidation, hydrolysis, enzymatic degradation, photodegradation, adsorption, denaturization, thermal degradation and physical degradation.

As presented herein, a breast milk collection and storage system has been developed to collect and store breast milk to achieve suckled quality milk.

BRIEF SUMMARY

Provided herein is a breast milk collection and storage system with a milk container operable to hold and store breast milk for an extended period of time. The milk container may include a container wall forming a container opening and an internal volume and a foil seal or resealable valve operable to seal the container opening. In some aspects, the container wall includes an oxygen blocking layer, a light blocking layer, and an inner surface that is non-adherent for lipids, proteins, and other hydrophobic moieties. In additional aspects, the milk container has low oxygen head space.

Further provided herein is a method for breast milk collection and storage. The method may include providing a milk container operable to hold and store breast milk for an extended period of time and filling the milk container with breast milk. In some aspects, the breast milk experiences a minimal increase in the concentration of lipid peroxides, photodegradation, and/or lipid and protein adsorption during the extended period of time.

Other aspects and iterations of the invention are described more thoroughly below.

BRIEF DESCRIPTION OF THE DRAWINGS

Implementations of the present technology will now be described, by way of example only, with reference to the attached figures, wherein:

FIG. 10A shows a milk bag with a cooling element docking area with recessions and a corresponding quick cooling element with ridges in one example.

FIG. 10B shows a milk bag with a cooling element docking area with recessions and assembled with a corresponding quick cooling element in one example.

DETAILED DESCRIPTION

Figure 1:
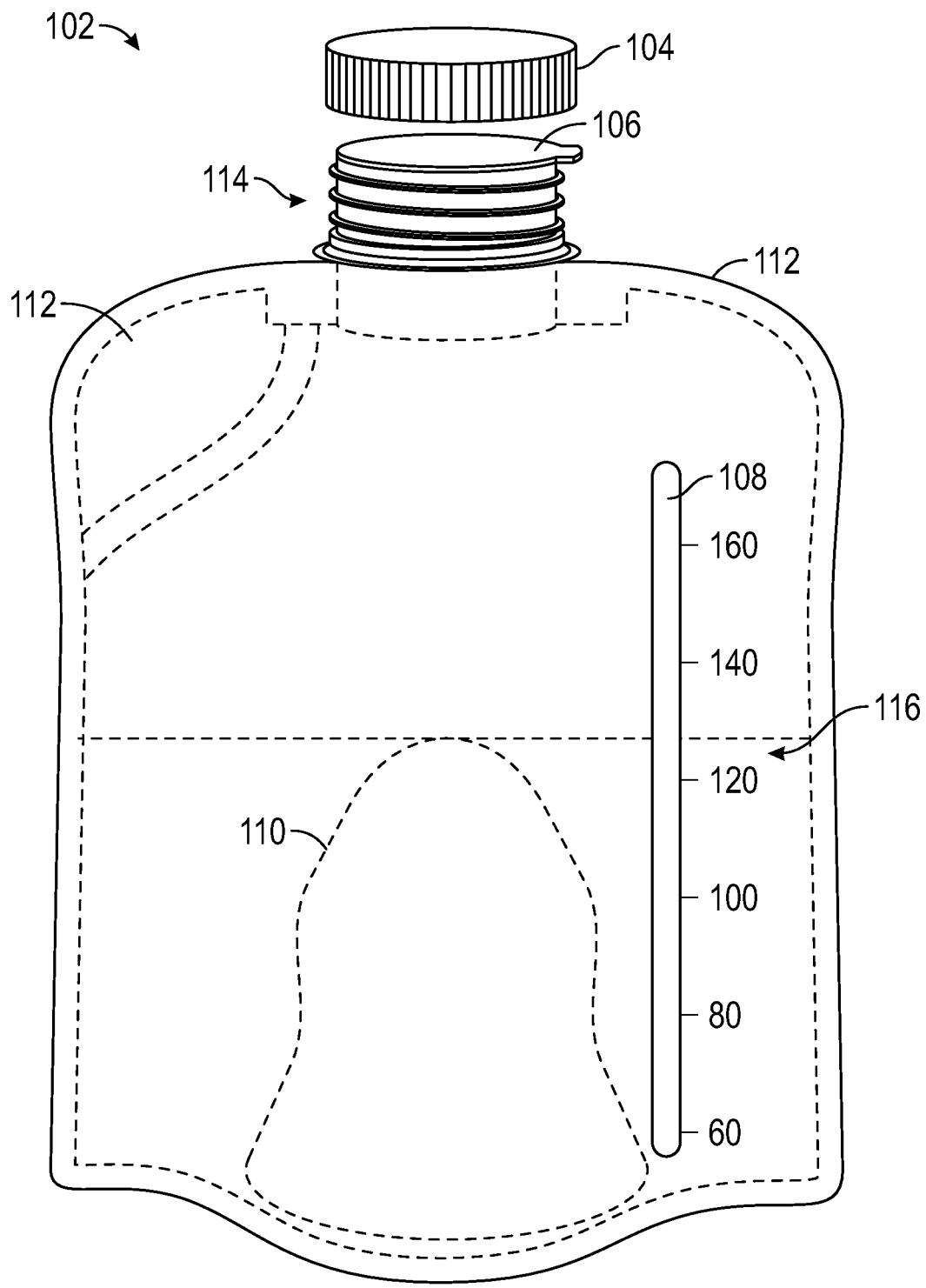
FIG. 1 shows a milk container as a milk bag in one example.

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout the above disclosure will now be presented. The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape or other word that substantially modifies, such that the component need not be exact. For example, "substantially cylindrical" means that the object resembles a cylinder, but can have one or more deviations from a true cylinder. The terms "comprising," "including" and "having" are used interchangeably in this disclosure. The terms "comprising," "including" and "having" mean to include, but not necessarily be limited to the things so described.

The term "breast milk" as used herein is defined as milk expressed from the breast of a human (i.e. suckled milk), human milk, and/or colostrum.

The term suckled quality milk is defined as expressed breast milk that maintains the chemical stability, nutritional benefits, physical structure, taste, microbial profile and purity of breast milk suckled directly into the mouth of the infant. Suckled quality milk maintains and prevents the degradation and loss of the diverse macro and micro nutrients, immune components, enzymes, growth factors and beneficial microbes without the creation or migration of harmful substances such as lipid peroxides and endocrine active molecules that can leach into the milk from most plastics including BPA free plastics.

In some examples, suckled quality milk maintains at least 70-100% of the most sensitive nutritional components known to degrade or adsorb rapidly during the storage and refeeding of expressed breast milk (EBM). In other examples, suckled quality milk has a total lipid peroxide concentration and/or vitamin B2 and A concentrations that are substantially similar to breast milk immediately after expression. For example, suckled quality milk is at least 60-100% identical in enzymatic content to milk provided to baby directly from the breast in real time. In some examples, suckled quality milk is at least 90-100% identical in lipid and lipid peroxide content to milk provided to baby directly from the breast in real time. In at least one example, suckled quality milk contains no/low endocrine active leachables as determined by endocrine binding assays and in vivo animal models.

The main constituents of colostrum and breast milk are water (87%), lipids (4%), lactose (7%), and the full spectrum of vitamins and minerals. It also contains many non-nutritive but growth/protective components such as signaling molecules, immune cells, antioxidants, oligosaccharides, milk fat globule membranes, hormones, growth factors, enzymes and other constituents. Breast milk has been reported to contain over 100,000 unique compounds. These compounds interact to protect the baby and provide the infant with optimal neuro, skeletal/muscular, immune system, and organ development.

Three of the most pressing problems faced by extremely low birth weight infants in the NICU are necrotizing enterocolitis leading to sepsis (NEC), retinopathy, and bronchopulmonary dysplasia (BPD). Breast milk has been found to improve outcomes for these conditions when compared to cow-based formula and fortifiers. The exact pathophysiology of NEC, retinopathy, BPD and sepsis are multifactorial but breast milk's TLR4 inhibition, epithelial growth factors, antioxidant properties, immune system modulating, ischemia preventing, and antimicrobial properties play key therapeutic roles in preventing these conditions and the lifelong morbidities that these conditions carry throughout life.

Conventional milk collection, storage, mixing and delivery methods and technologies do very little to protect the myriad of components in fresh breast milk that are subject to degradation. For example, many key TLR4 inhibiting molecules shown to help prevent NEC, such as Vitamins A, B2, D, and/or glycine, are easily degraded by oxidation or photodegradation. Further, antioxidants such as vitamins C, E and A, carotenoids and glutathione rapidly react with air once pumped into an air filled container and stored.

Once the antioxidant system of milk is depleted then the polyunsaturated fatty acids can degrade rapidly by both hydrolysis and oxidation. Free fatty acids that are oxidized are highly inflammatory and have been shown to be cytotoxic to lymphocytes.

Forty percent of the calories of the milk are provided by the fat content in breast milk. Plastic containers are typically made from lipophilic polymers which will adsorb fat on the surface. Nasogastric tubes used to feed NICU infants are also made from lipophilic materials. During storage and feeding delivery to the baby up to 40% of the lipid content can be lost in to adsorption or physical instability. Furthermore, milk proteins and peptides have hydrophobic and hydrophilic regions that can adhere and adsorb to the surface of the container.

The breast milk collection and storage system is a unique and novel system to collect, store, and feed breast milk to achieve suckled quality milk for baby. The system consists of flexible and rigid collection containers that attach direct to the breast pump, have an oxygen free headspace, oxygen and photo barrier construction such that there are no or low endocrine active leachates, an internal rapid cooling capability, and the capability to transfer, feed or fortify the breast milk in a closed system to prevent degradation, adsorption, and contamination.

Figure 2:
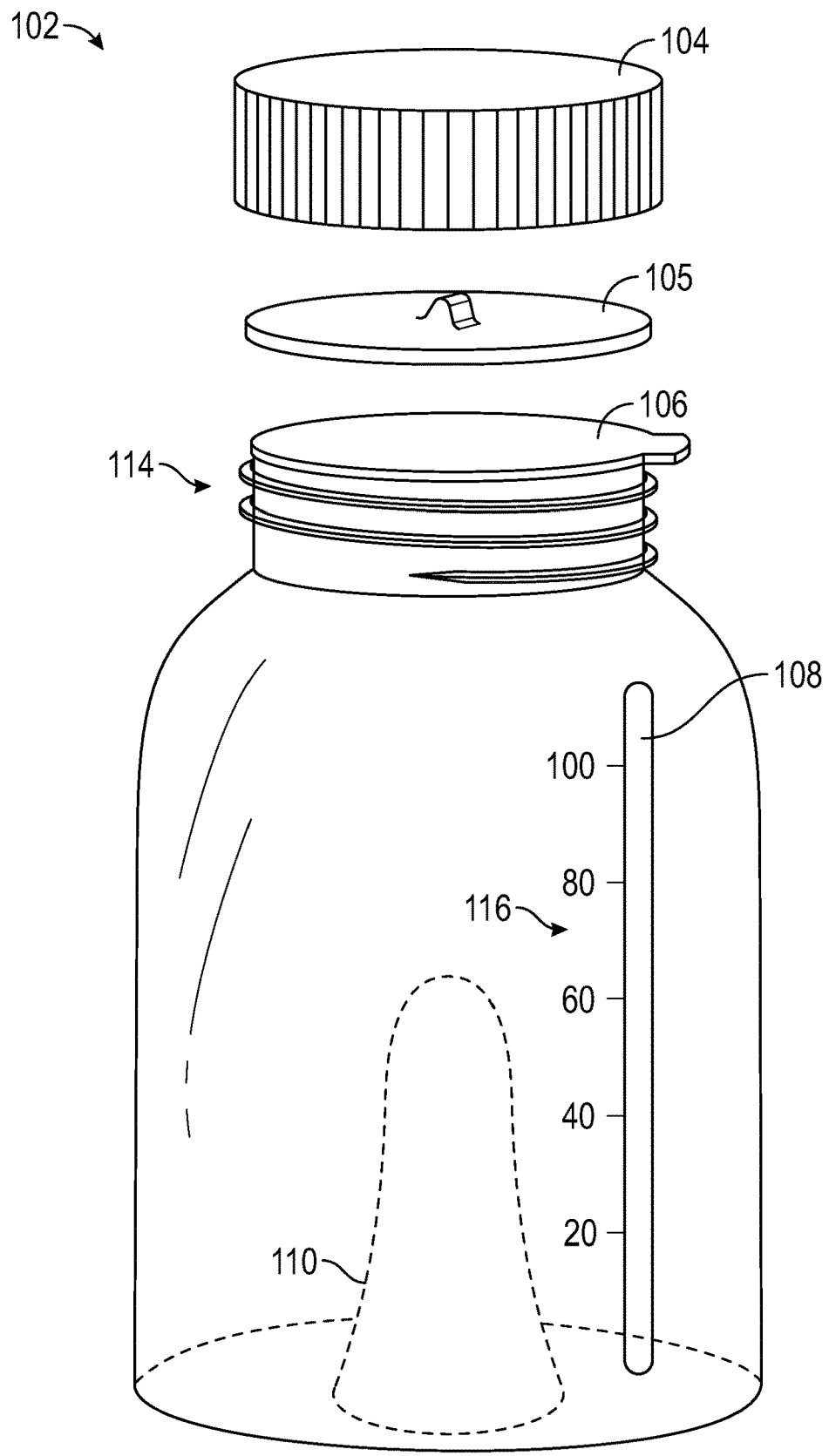
FIG. 2 shows a milk container as a milk bottle in one example.

Referring to FIGS. 1 and 2, the breast milk collection and storage system may include a milk container 102. The milk container may be operable to collect and store breast milk and/or colostrum. In some examples, the milk container is a flexible wall container or a rigid container. In additional examples, the milk container is a bag or a bottle. The shape of the milk container may shaped in any way such that it may be compatible with a commercial pumping system. FIG. 1 shows an example milk container 102 as a flexible milk bag. In yet another example, the milk container may be an O-shaped milk bag for use with a wearable breast pump. In some examples, the milk bag may remain flexible at 0° C. or lower temperatures. FIG. 2 shows an example milk container 102 as a rigid milk bottle. As seen in FIGS. 1 and 2, the milk container 102 may further include a cap 104, a foil seal 106, a milk volume window 108, a cooling element docking area 110, and a labeling area 112. In some examples, the milk container 102 may also include a lid 105 between the cap 104 and the foil seal 106.

The milk container 102 has a container wall 112 that forms an internal volume around an opening 114. The milk container may have an internal volume of at least 1 oz, at least 2 oz, at least 3 oz, at least 4 oz, at least 5 oz, at least 6 oz, at least 7 oz, at least 8 oz, at least 9 oz, or at least 10 oz. In other examples, the milk container may have an internal volume of at least 20 ml, at least 40 ml, at least 60 ml, at least 80 ml, at least 100 ml, at least 120 ml, or at least 140 ml. In some examples, the milk container may provide volume markings 116 on the outer surface of the container to indicate the volume levels, such that a user can determine the volume of milk within the container.

The milk container may further include a milk volume window 108. The milk volume window may provide the user ease of access in viewing the level of milk within the container to determine the volume. In some examples, the milk volume window is a transparent or semi-transparent strip extending along the length of the volume markings, as seen in FIGS. 1 and 2. The milk container may further include a labeling area 112 for labeling the milk container, for example, with the date and/or time of milk expression, volume of milk in the milk container, name, etc.

Because components of the breast milk degrade in quality due to oxidation, the milk container of the breast milk collection and storage system may have low oxygen head space as compared to a typical milk collection container. The internal volume of the milk container may have 4% or less of oxygen prior to being filled with milk. For example, the milk container may be pre-filled with an inert gas and the sealed such that it contains minimal or no oxygen prior to being filled with milk. The flexible milk container may be pre-filled with 100 cc or less of the inert gas. The rigid milk container may be pre-filled with an amount of the inert gas that fills the entire container. Non-limiting examples of the inert gas include $N_2$, Ar, and $CO_2$. The milk container may be operable to maintain the low oxygen headspace during and after filling the milk container with expressed breast milk. The internal volume of the milk container may have 10% or less of oxygen after being filled with milk.

The milk container 102 may further include a foil seal 106 attached to the opening 114 of the milk container 102 to maintain the low oxygen head space within the internal volume of the milk container. In an example, a foil seal may be operable to seal the milk container prior to use to prevent external oxygen from entering the container. The foil seal 106 may include foil on a polymer attached to the opening 114 of the milk container. The container wall 112 of the milk container 102 may further include an oxygen barrier to limit oxidation of the milk stored in the container. For example, the milk container may include a layer that is impermeable to oxygen, such that oxygen cannot seep into the milk container prior to or after filling the container with milk. Non-limiting examples of oxygen impermeable polymers include ethylene vinyl alcohol (EVOH), polyamide (PA), polyethylene terephthalate (PET), foils, BOPP/BOPP nanolayers, silica, or similar oxygen barriers. Materials with high oxygen transfer rates are not desirable such as polyethylene (PE), polyester and silicone on their own without one or more barrier layers.

Because components of the breast milk degrade in quality due to photodegradation, the container wall 112 of the milk container 102 may further have a light barrier. In some examples, the light barrier may make the milk container opaque or brown in color. The light barrier may be any material capable of blocking light by at least 90%. For example, the light barrier may block at least 90% of light in the blue and UV wavelengths. The light barrier may contain light blocking polymers, structures, and/or additives. Non-limiting examples of light blocking polymers, structures, and additives include inorganics such as metal foils or particles of metal oxides, and organics such as salicylates. In some examples, the light barrier may be an opaque shrink wrap applied to the external surface of the container wall.

In some examples, the oxygen barrier and light barrier layers of the container wall may be formed by multilayer co-extrusion, thin film deposition, lamination, or may be alloyed into the base polymer. In at least one example, the container wall may include a pleated oxygen and light barrier.

Because the lipid and protein constituents of the breast milk are important for the baby, the milk collection and storage system should not adhere or remove a significant amount of lipids or proteins from the collected and stored breast milk. The milk container and/or all milk contacting surfaces of the breast milk collection and storage system may include low lipid and protein binding surfaces such as high gloss polypropylene (PP), polyethylene terephthalate (PET), polyethylene oxide (PEO), or other polyolefins. The milk container and/or the milk contacting surfaces do not include higher surface energy polymers such as polyvinyl chloride (PVC) and polyurethane, as they tend to absorb lipids to the surface. For example, the milk container may include an inner surface that is non-leaching, low extractable, and/or non-adherent for lipids, proteins, and/or other hydrophobic moieties. In some examples, the inner surface of the container wall may be hydrophilic. The inner surface of the container wall may be operable to adsorb less than 40%, less than 30%, less than 20%, less than 10%, or less than 5% of the lipid content in the breast milk. In an example, the milk contacting surface of the milk container may include polymers from the polyolefin class with minimal processing additives such as blocking agents, anti-caking agents, nucleating agents, slip agents, UV blocking agents, and/or antioxidants. In this example, the milk container may have no or low endocrine active leaching substances.

Figure 3A:
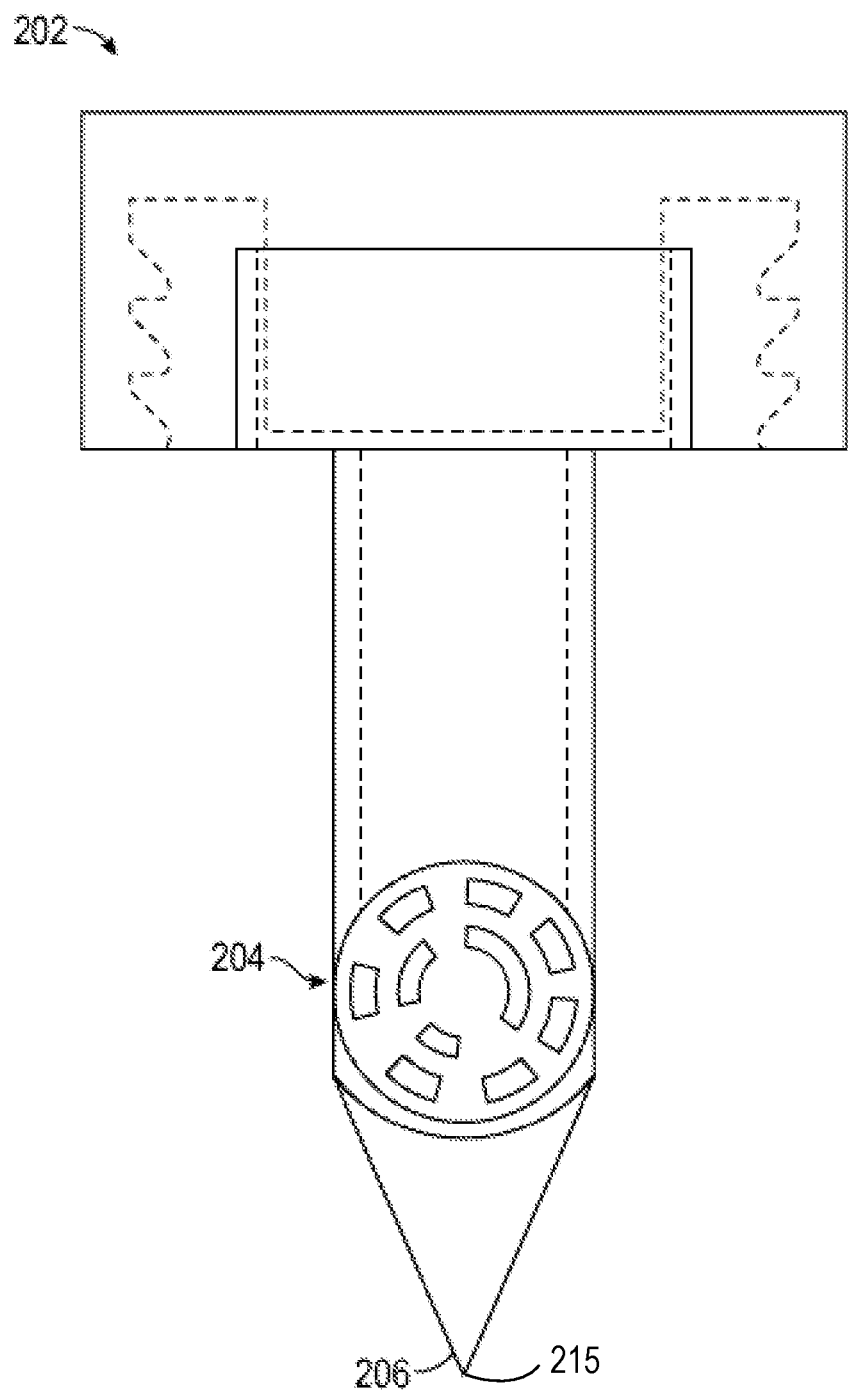
FIG. 3A shows a piercing flapper valve in one example.
Figure 3B:
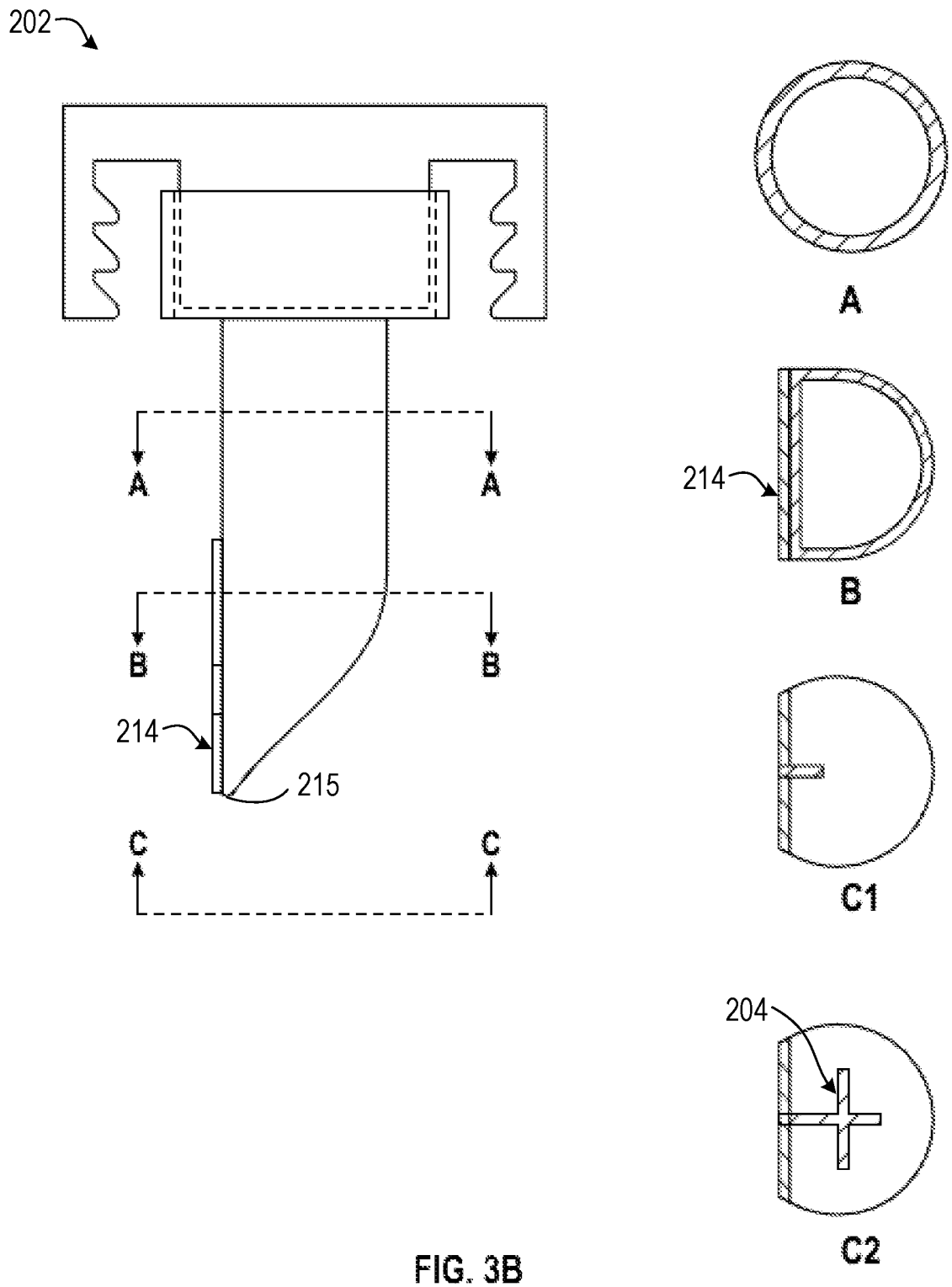
FIG. 3B shows a piercing flapper valve with multiple cross sections in one example.

The breast milk collection and storage system may further include a piercing flapper valve 202 or check valve. In an example, the piercing flapper valve may be operable to pierce the foil seal on the milk container. Referring to FIGS. 3A and 3B, the breast milk collection and storage system may include a foil piercing flapper valve with different piercing geometries. FIG. 3A shows a view of the piercing flapper valve 202 with the flapper 204 on the side of the body of the flapper valve, above the piercing tip 206. In some examples, the flapper valve may include a flapper inversion prevention feature 214 at the lower lip 215 of the flapper valve to prevent the flapper valve from inverting during puncture of the foil seal into the bottle or bag. FIG. 3B shows multiple cross sections of the piercing flapper valve 202 to show the lower lip 215 and the flapper 204. In some examples, the flapper may be recessed as compared to the lower lip, thus forming the flapper valve inversion feature.

Figure 4:
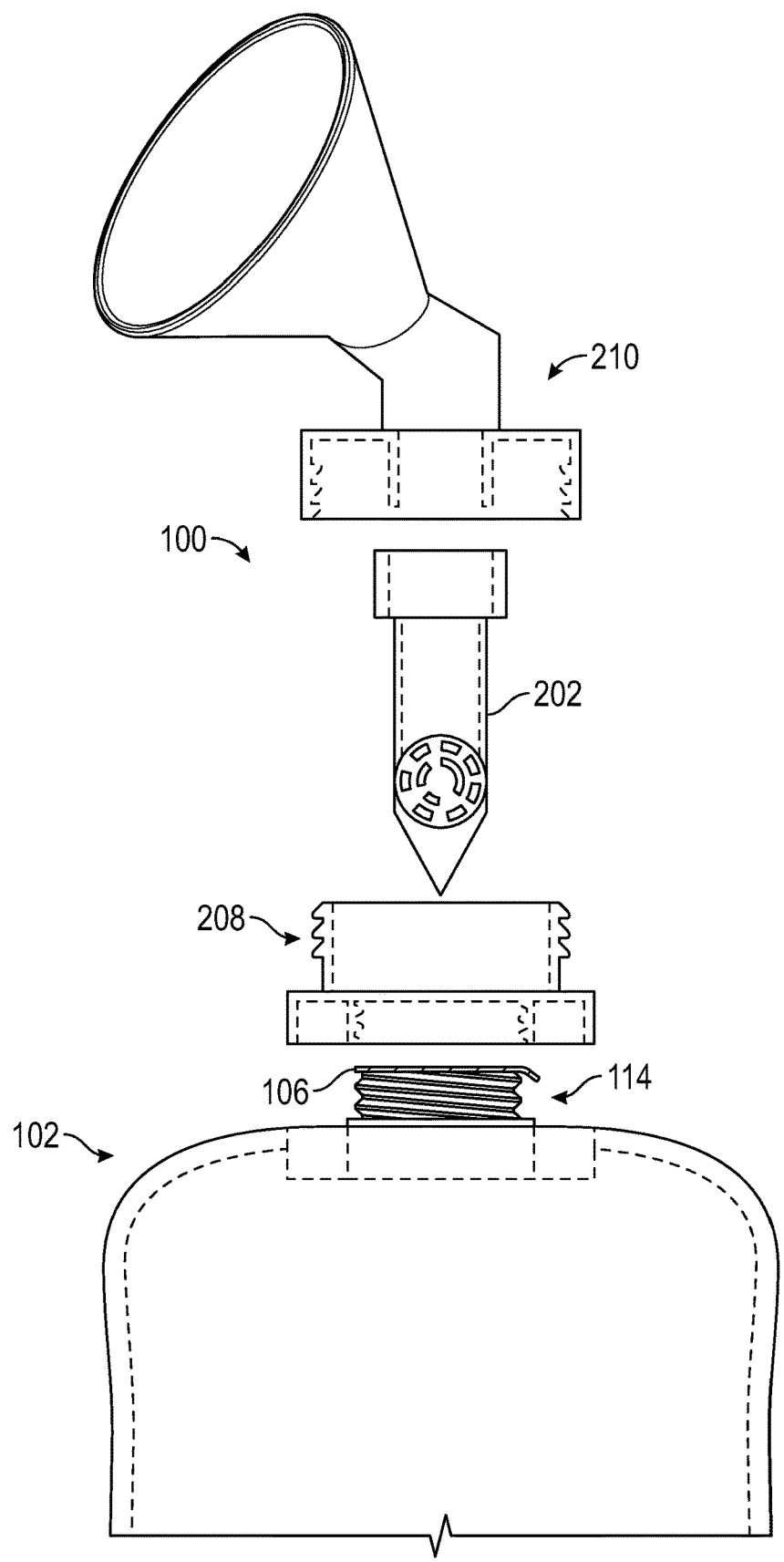
FIG. 4 shows a breakout view of the breast milk collection and storage system in one example.
Figure 5:
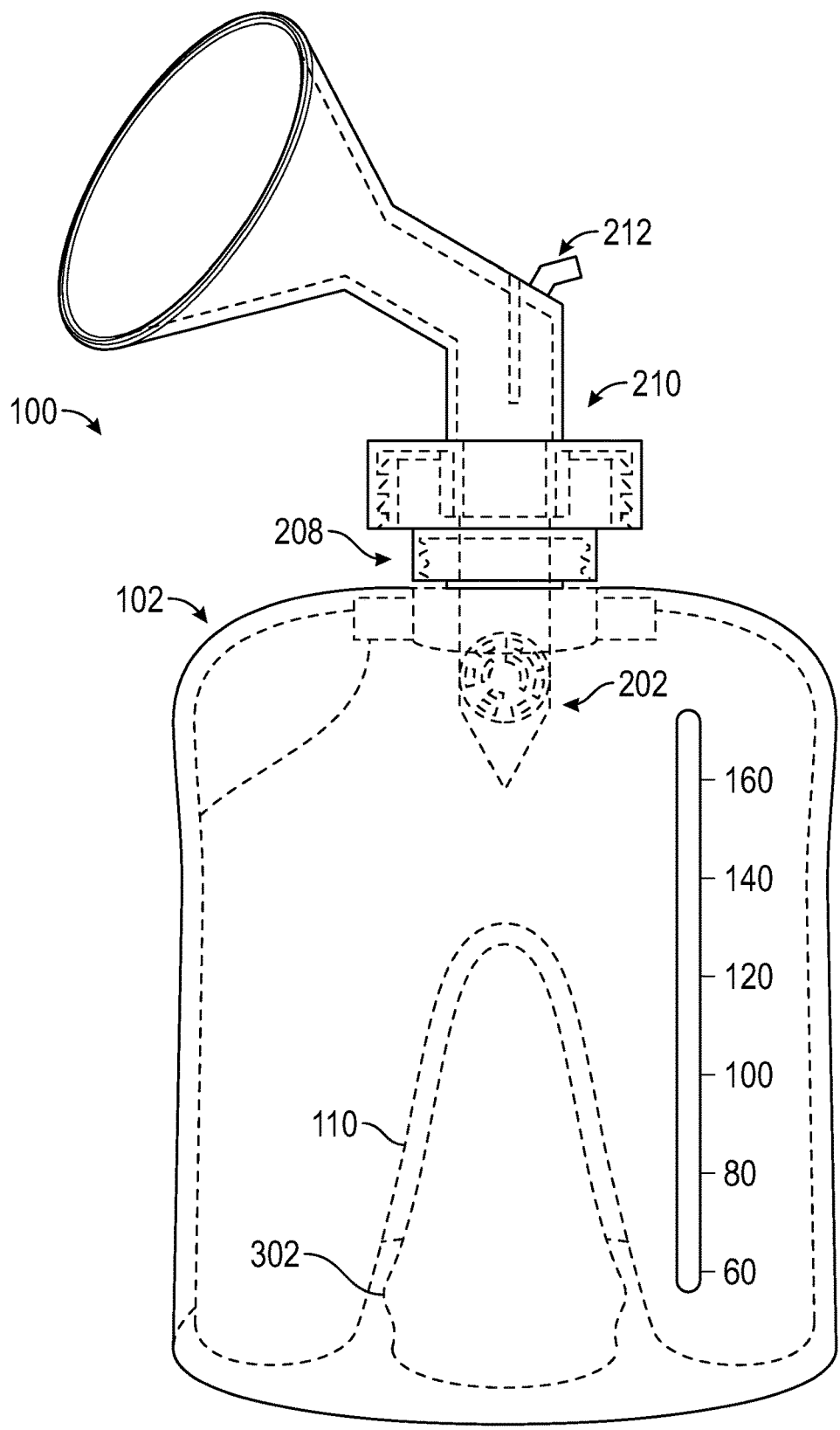
FIG. 5 shows an assembled breast milk collection and storage system in one example.

FIG. 4 is a breakout view and FIG. 5 is an assembled view of the breast milk collection and storage system 100. In an example, the breast milk collection and storage system 100 may include a milk container 102 having a foil seal 106 sealing the container and an inert headspace containing $N_2$, Ar, or $CO_2$ within the milk container, a piercing flapper valve 202, and a flange body adapter 208. Although the milk container 102 is depicted as a flexible bag, the milk container may also be a bottle. The inert gas may be prefilled in the entire milk container or in the headspace of the milk container. Alternatively the milk container may have an attachment from which the user can add gas into the milk container during or after the pumping session.

Figure 6:
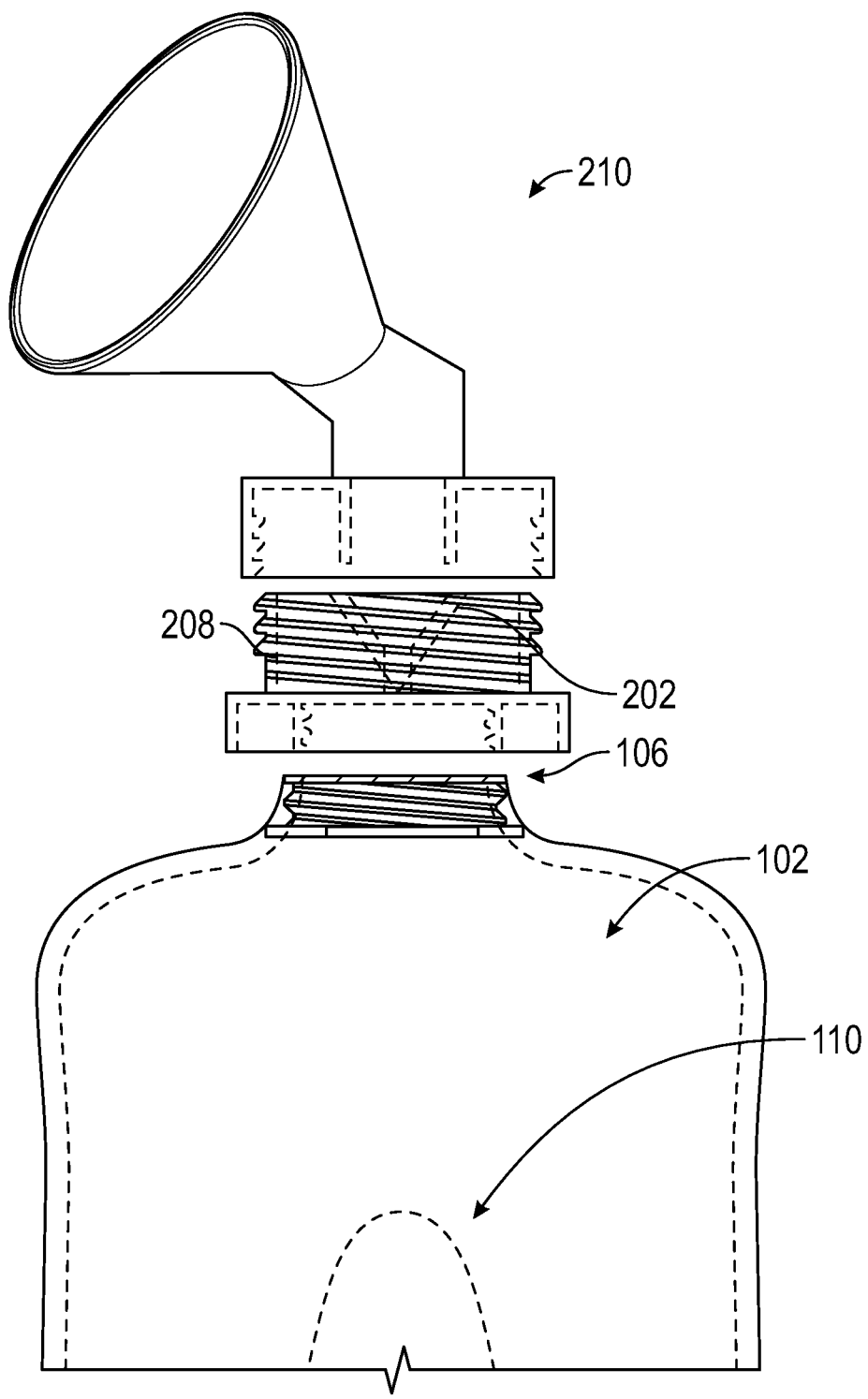
FIG. 6 shows a breakout view of an alternative breast milk collection and storage system in one example.

As seen in FIGS. 5 and 6, the breast milk collection and storage system 100 provides for direct pumping into the oxygen free flexible milk container using the piercing flapper or check valve 202. Use of the piercing flapper or check valve may allow for maintaining the oxygen free or low oxygen environment within the milk container, such that the components of the breast milk may have limited exposure to oxygen. For example, by pre-sealing the milk container with low oxygen head space and then using the flapper valve to pierce the foil seal, the components in the milk may experience minimal oxidation while being stored in the milk container as compared to standard milk collection systems. Alternatively, a user may add inert gas from an attached separate container during or immediately after pumping to create the low oxygen or no oxygen environment.

The breast milk collection and storage system may be operable to connect to or be compatible with any commercial or hospital grade breast pump. Non-limiting examples of commercial pumps the breast milk collection and storage system is compatible with includes Medela®, Ameda®, Spectra®, Evenflo®, Lansinoh®, Willow®, Elvie™, Freemie®, etc. In various examples, the breast milk collection and storage system 100 includes a flange body adapter to aid in connecting the breast pump, such as a breast pump flange valve, to the milk container. As seen in FIGS. 4 and 5, a breast pump flange body 210 of any commercial or hospital grade breast milk pump may reversibly connect to the piercing flapper or check valve 202 and/or the flange body adapter 208. The breast pump flange body 210 may include a vacuum port 212 that may be reversibly connected to the breast pump. The flange body adapter 208 may reversibly attach to a breast pump flange 210 at one end and reversibly attach to the milk container 102 at a second end. The flange body adapter 208 body forms an opening between the first and second end operable for receiving the flapper valve or check valve 202. FIG. 6 shows a flange-to-milk container piercing check valve adapter, which includes an alternative flange body adapter 208 with an integrated piercing check valve 202. The integrated piercing check valve 202 may be an integrated silicone/TPE valve. In this example, the piercing check valve 202 may be fully contained within the flange body adapter 208. The piercing check valve 202 may be a flexible check valve inside a piercing cone. The flange-to-milk container piercing check valve adapter may be over molded or may be two pieces connected together. A breast pump flange body 210 may reversibly connect to the flange body adapter 208 with the integral piercing check valve 202. The flange body adapter 208 may reversibly attach to a breast pump flange 210 at one end and reversibly attach to the milk container 102 at a second end, with the piercing check valve 202 in the opening between the first and second ends of the flange body adapter 208. In some examples, the breast milk collection and storage system 100 includes low lipid binding tubes (ex. NG tubes) and/or syringes which may replace parts of a commercial pump system.

Figure 7:
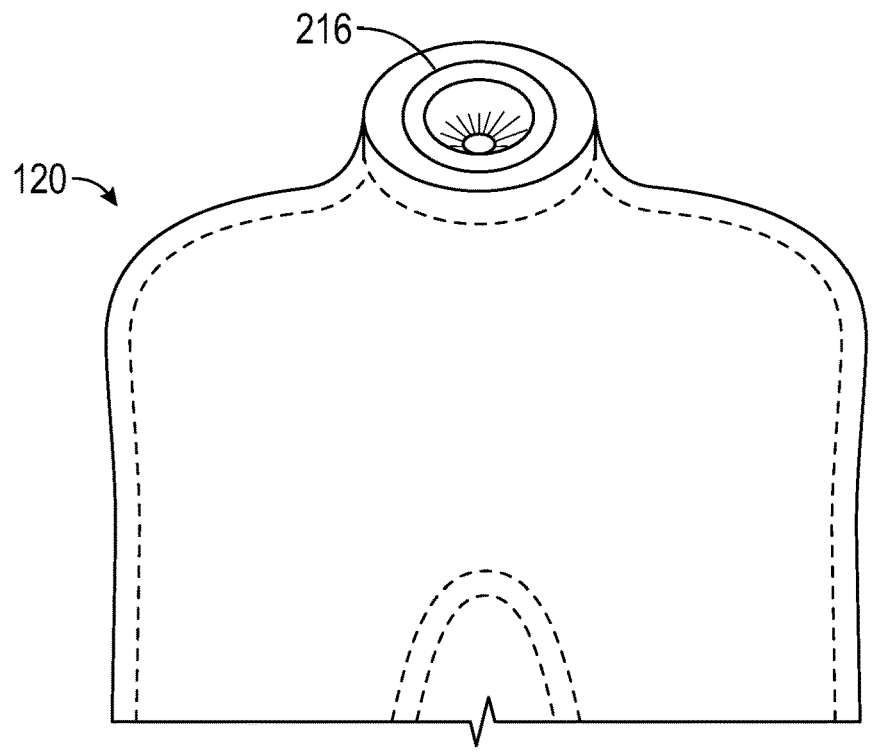
FIG. 7 shows a view of an alternative breast milk collection and storage system with an integral valve in one example.
Figure 8:
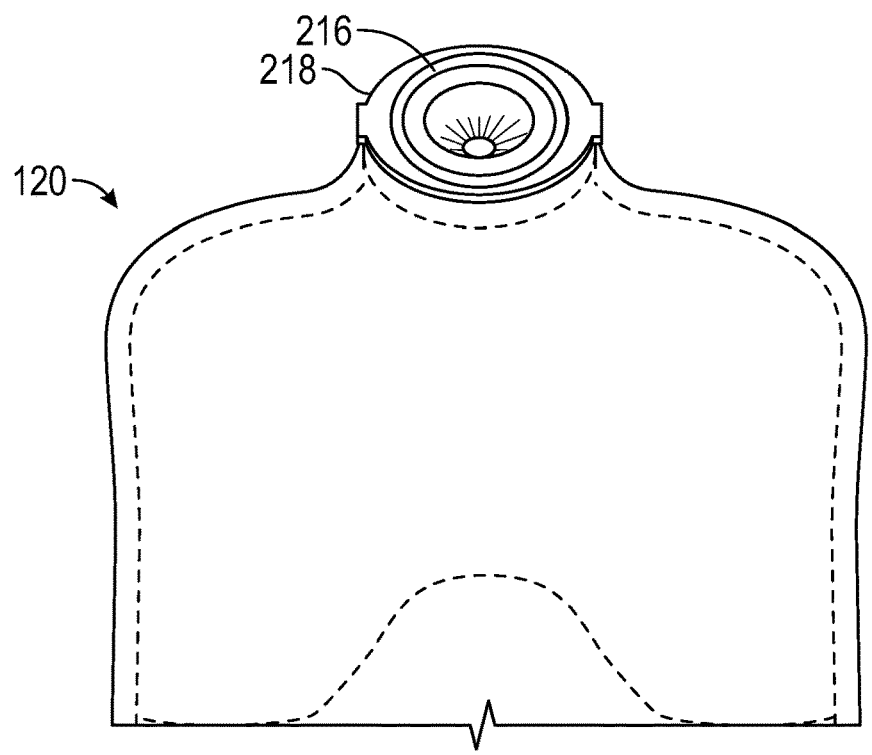
FIG. 8 shows a view of an alternative breast milk collection and storage system with an integral valve in one example.

Alternatively, a milk container may not include a foil seal but instead include a resealable valve. FIG. 7 shows an alternative milk container 102 with an integral and resealable valve 216. In some examples, the integral valve 216 may be made of silicone or thermoplastic elastomers (TPE). FIG. 8 shows an optional overmolded locking ring 218 that may act as a coupler adapter. In these examples, the breast milk collection and storage system 100 may not include a piercing flapper or check valve because the integral valve 216 is resealable.

The degradation reactions in milk are temperature dependent. Therefore, it is important to cool breast milk to about 2° C. to about 8° C. immediately or as soon as possible after it is expressed. In an example, the breast milk collection and storage system 100 may further include a quick cooling apparatus 300. In some examples, the quick cooling apparatus 300 may have at least one quick cooling element 302. The quick cooling element may be loose or fixed within the quick cooling apparatus.

The quick cooling element may have a rigid or semi-soft plastic wall. The quick cooling element may be filled with a cooling material. In some examples, the cooling material may be a water or water based gel, hydrogels of propylene, super absorbent polymers (SAP), cellulose, carboxymethylcellulose, EMA, and/or PVA. The quick cooling element may be operable to provide large surface area contact of the cooling material to the breast milk stored in the milk container.

Figure 9A:
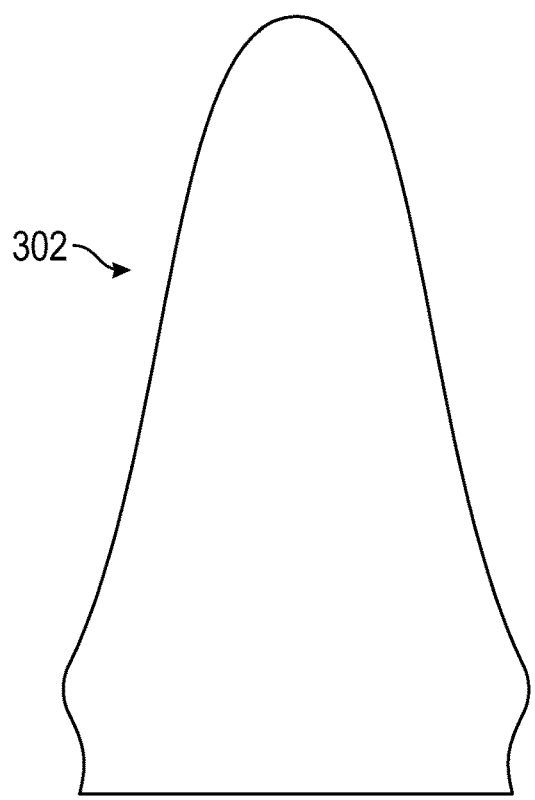
FIG. 9A shows a quick cooling element in one example.
Figure 9B:
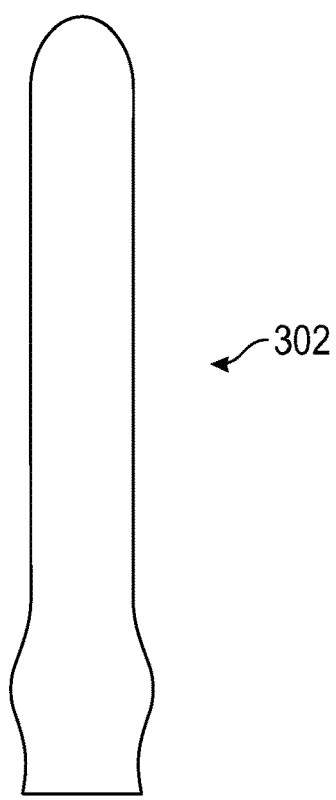
FIG. 9B shows a quick cooling element in one example.
Figure 9C:
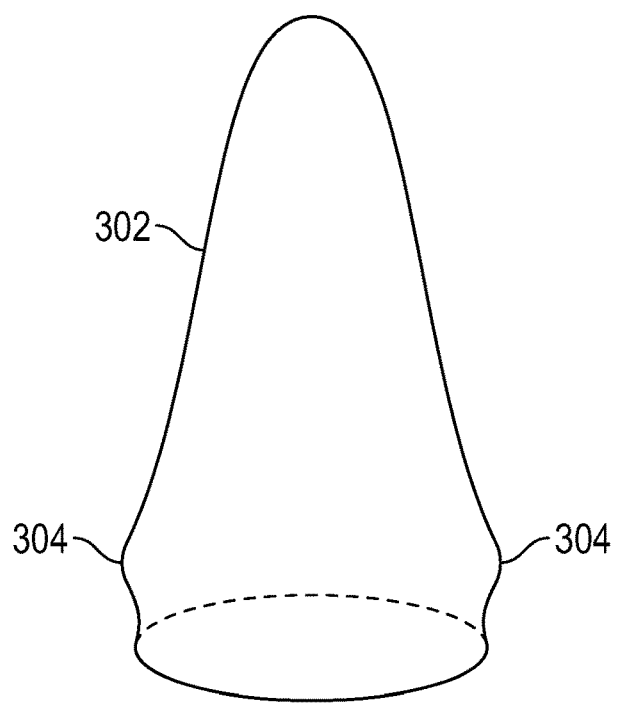
FIG. 9C shows a quick cooling element in one example.
Figures 11A, 11B:
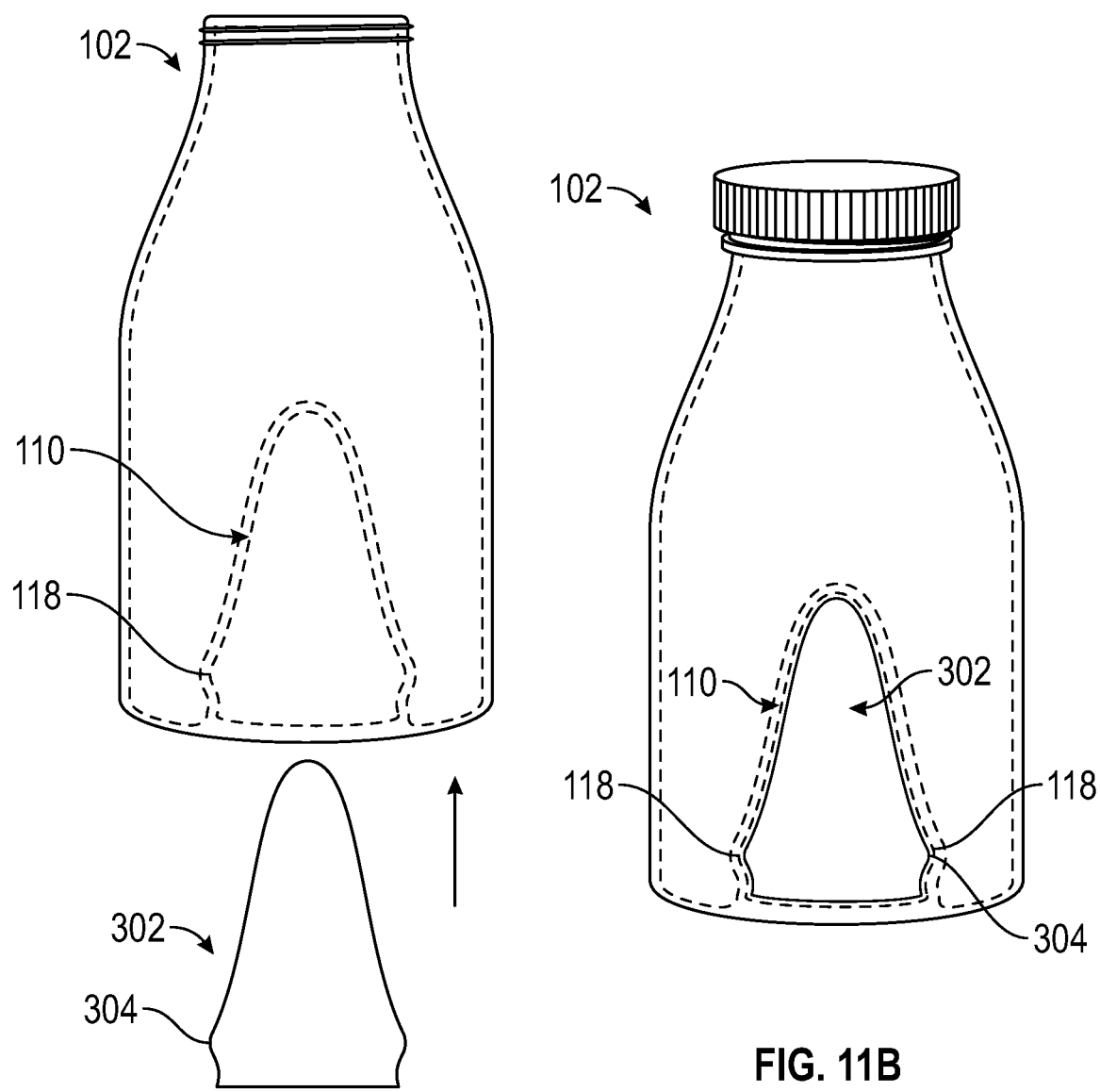
FIG. 11A shows a milk bottle with a cooling element docking area with recessions and a corresponding quick cooling element with ridges in one example.
FIG. 11B shows a milk bottle with a cooling element docking area with recessions and assembled with a corresponding quick cooling element in one example.
Figure 12:
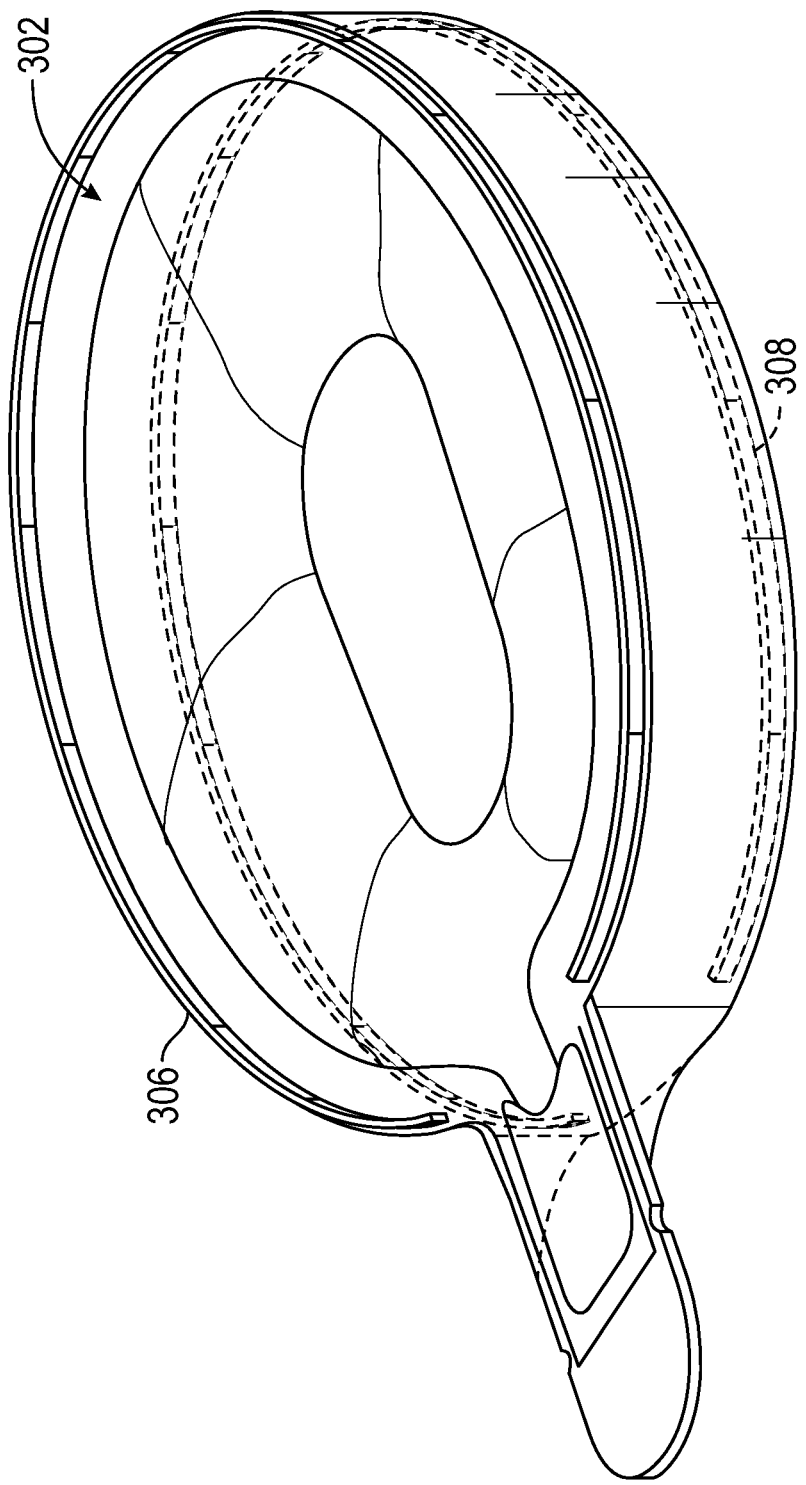
FIG. 12 shows an O-shaped quick cooling element in one example.

FIGS. 9A-9C show example quick cooling elements and FIGS. 10A-10B and 11A-11B show a quick cooling element 302 within the breast milk collection and storage system 100. The quick cooling element may be a projection or prong for receiving the milk container as, for example, in FIGS. 9A-9C. In other examples, the quick cooling element may be flat and shaped to provide contact with the surface of one side of a milk container. The shape of the quick cooling element may vary depending on if the milk container is a bag or a bottle and may vary depending on the shape of the bag. The shape of the quick cooling element may also vary to match the shape of the perimeter of the cooling element docking area of the milk container. In an example, as seen in FIGS. 1, 2, 5, 10A, and 11A the milk container 102 includes a cooling element docking area 110 at the bottom of the milk container, operable to releaseably receive the quick cooling element 302. In an example, the cooling element docking area may be a recession in the milk container such that most or all of the quick cooling element fits inside the docking area and allows for increased surface area contact between the contents of the container and the quick cooling element. FIGS. 10A and 11A show an assembled view of the breast milk collection and storage system with the quick cooling element within the cooling element docking area. The quick cooling element is shaped to fit securely within the cooling element docking area. In an example, the quick cooling element 302 may include ridges 304 operable to anchor or provide a "click-in" attachment to corresponding recessions 118 in the cooling element docking area 110 of the milk container 102, as seen in FIGS. 10B and 11B. In another example, the quick cooling element 302 may be O-shaped to substantially match an O-shaped milk container, as seen in FIG. 12. The O-shaped cooling element may include a stacking mechanism for facilitating the connection and stacking of multiple O-shaped cooling elements. For example, the O-shaped cooling element may further include a tongue and groove for stacking two or more O-shaped cooling elements. The O-shaped cooling element may include a tongue or ridge around the circumference of the top of the cooling element and a groove around the circumference of the bottom of the cooling element, such that the tongue of a first O-shaped cooling element fits into the groove of a second O-shaped cooling element stacked on top of the first O-shaped cooling element.

Figure 13:
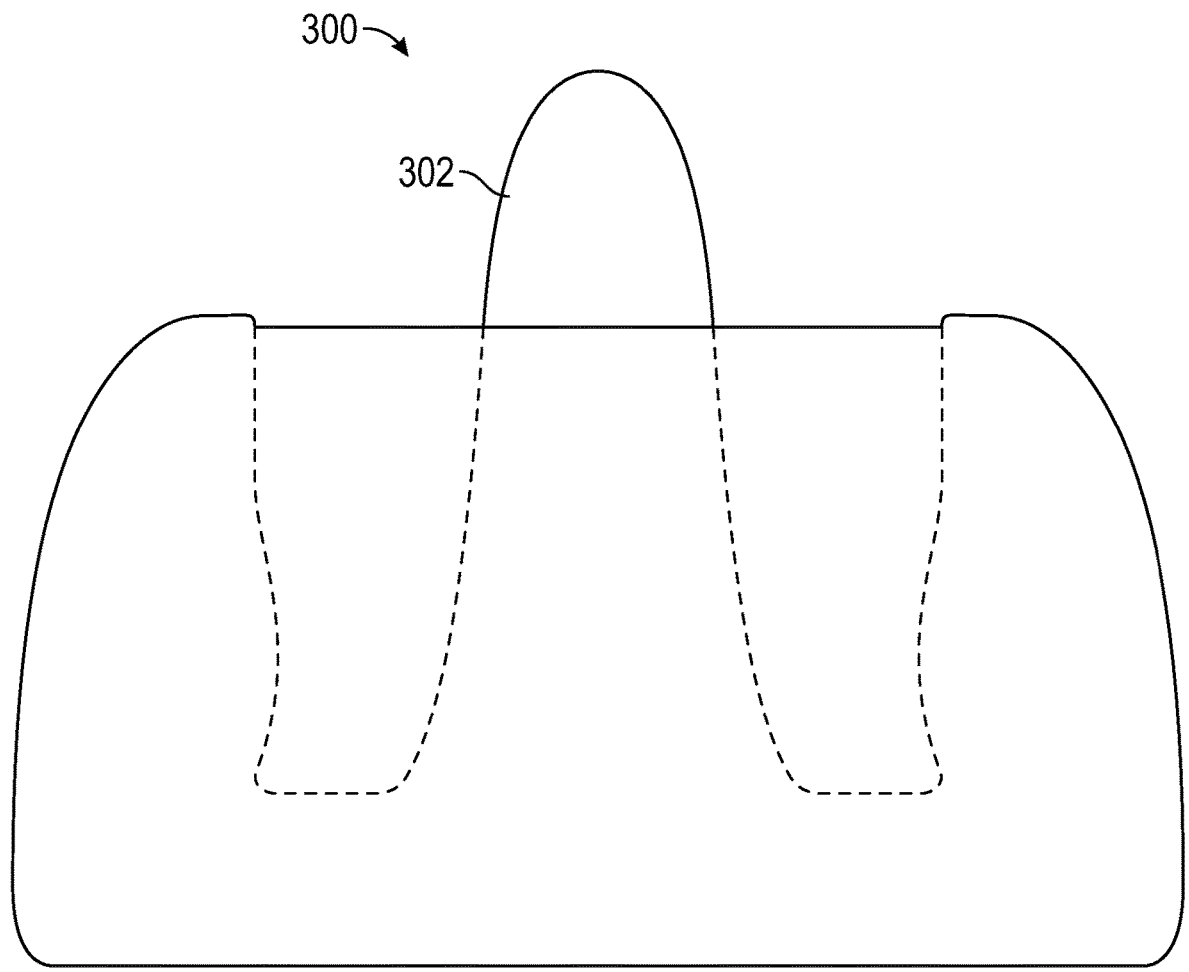
FIG. 13 shows a quick cooling apparatus with one quick cooling element in one example.

In some examples, the quick cooling apparatus includes at least one quick cooling element, where the projection of the quick cooling element is further surrounded by at least two recessions for receiving the bottom of the milk container, as seen in FIG. 13. This may allow the milk container to be further secured or attached to the quick cooling element.

Figure 14:
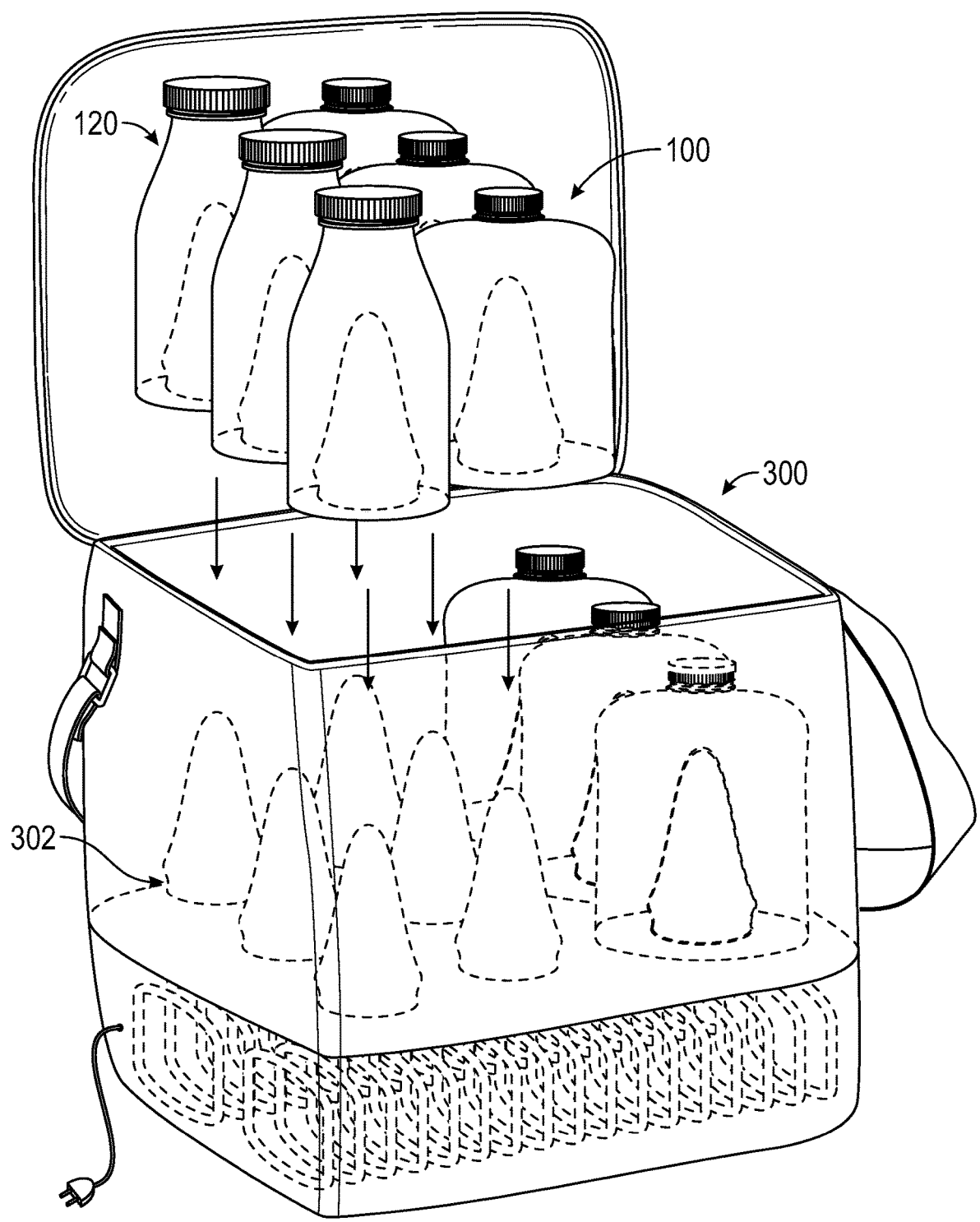
FIG. 14 shows a quick cooling apparatus with multiple quick cooling elements in one example.

In some examples, the quick cooling apparatus 300 includes more than one quick cooling element 302. For example, as seen in FIG. 14, the quick cooling apparatus 300 may be an integrated cooler box or bag with a series of quick cooling elements 302 for cooling more than one milk container at the same time. The quick cooling elements may be arranged on the bottom surface of the box or bag. In some examples, the quick cooling elements may be fixed or reversibly attached to the bottom surface. For example, quick cooling elements may be removed and/or replaced if needed. In some examples, the quick cooling apparatus may include a carry strap or other means for easily carrying the box/bag. In an example, the box or bag may be opaque, insulated, rigid, and/or soft sided. The quick cooling apparatus may include an electric cooling base operable to cool the quick cooling elements. In some examples, the quick cooling apparatus may include a power connector for providing electric power to the electric cooling base and quick cooling elements. In another example, the electric cooling base may be detachable. In some examples, the quick cooling apparatus includes a cooling element operable to be frozen prior to use. In other examples, the quick cooling apparatus includes at least one battery to power the quick cooling elements. The battery may be disposable or rechargeable.

The quick cooling element may reduce the temperature of the expressed breast milk to a temperature of about 2-8° C. within about 5 minutes after expression. Many enzymatic and degradation reactions in milk and colostrum are temperature dependent. Lipase is an enzyme that helps break down fat for improved absorption. However, in expressed breastmilk, extended lipase reactions at room temperature can significantly alter the taste of the milk for baby.

In various examples, a suckled composition or suckled quality milk refers to breast milk/colostrum stored in the milk container provided herein. The milk container holds expressed breast milk having a composition that is suckled quality after up to 12 days or more of storage in a refrigerator. For example, the breast milk collection and storage system may provide suckled quality milk up to 1 day, 2 days, 3 days, 4 days, 5 days, 6 days, 7 days, 8 days, 9 days, 10 days, 11 days, 12 days or more after storage at 2-8° C. For example, the breast milk collection and storage system may provide suckled quality milk up to 7 days after storage at 2-8° C. Providing baby with milk that has not been frozen and thawed can prevent the destabilization of the fat globules which retains their digestability.

Figure 15:
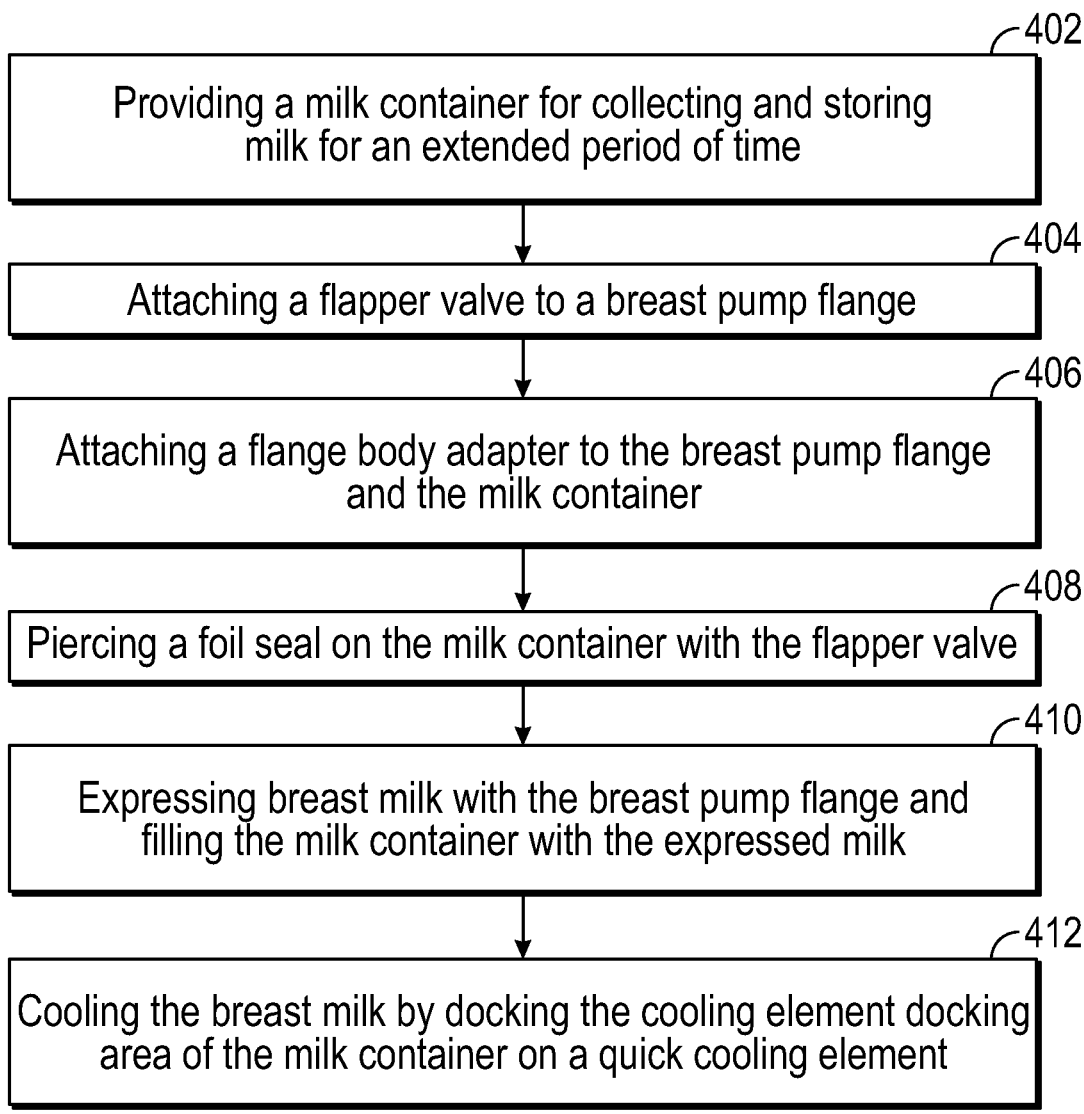
FIG. 15 is a method for collecting and storing breast milk in one example.

Further provided herein are methods of collecting and storing breast milk. Referring to FIG. 15, a flowchart is presented in accordance with an example embodiment. The method 400 is provided by way of example, as there are a variety of ways to carry out the method. The method 400 described below can be carried out using the configurations illustrated in FIGS. 4-8, 10A, and 14, for example, and various elements of these figures are referenced in explaining example method 400. Each block shown in FIG. 15 represents one or more processes, methods or subroutines, carried out in the example method 400. Furthermore, the illustrated order of blocks is illustrative only and the order of the blocks can change according to the present disclosure. Additional blocks may be added or fewer blocks may be utilized, without departing from this disclosure.

The example method 400 is a method of collecting and storing breast milk in a milk container for an extended period of time. The example method 400 can begin at block 402. At block 402, a milk container for collecting and storing milk for an extended period of time is provided. Use of the milk container to collect and store the breast milk may limit oxidation, photodegradation, physical instability, and/or lipid adsorption of the milk. In some examples, the breast milk experiences a less than 10% increase in the concentration of lipid peroxides, photodegradation, and/or lipid adsorption during the extended period of time. In some examples, the physical milk structure remains intact for 4-14 days when stored at 2-8° C. In at least one example, the milk container includes a container wall having an oxygen blocking layer, a light blocking layer, and an inner surface that is non-adherent for lipids, proteins, and/or other hydrophobic moieties; a container opening surrounded by the container wall; and a foil seal operable to seal the container opening. In some examples, the milk container has low oxygen head space.

At block 404, a flapper or modified check valve is attached to a breast pump flange. In an example, the breast pump flange is attached to a breast pump.

At block 406, a flange body adapter is attached to the breast pump flange and the opening of the milk container. In an example, the flange body adapter has a first end that attaches to the breast pump flange and a second end that attaches to the milk container. In at least one example, the flapper valve may be received through an opening in the flange body adapter formed between the first end and the second end.

At block 408, the foil seal on the milk container is pierced by the flapper valve. In an example, the flapper valve includes a lower lip operable to prevent the flapper valve from inverting when piercing the foil seal.

At block 410, breast milk is expressed with the breast pump flange and breast pump such that the milk container is filled with expressed breast milk.

At block 412, the breast milk in the milk container is cooled by docking the cooling element docking area of the milk container on a quick cooling element. In an example, the quick cooling element may be in a quick cooling apparatus. In at least one example, the quick cooling apparatus may include more than one quick cooling element.

The method may further include storing the breast milk in the milk container for an extended period of time while maintaining suckled quality milk. The extended period of time may be at least 1 day, at least 2 days, at least 5 days, at least 7 days, at least 10 days, or at least 12 days. Alternatively, the extended period of time may be up to 1 day, up to 2 days, up to 3 days, up to 4 days, up to 5 days, up to 6 days, up to 7 days, up to 8 days, up to 9 days, up to 10 days, up to 11 days, or up to 12 days. The breast milk stored in the milk container may be suckled quality after up to 12 days of storage in a refrigerator. For example, the method includes storing the breast milk container at 2-8° C. up to 1 day, 2 days, 3 days, 4 days, 5 days, 6 days, 7 days, 8 days, 9 days, 10 days, 11 days, or 12 days after storage and providing suckled quality milk. In at least one example, the method includes storing breast milk in a milk container for up to about 7 days in the refrigerator (i.e. about 2-8° C.) and providing the suckled quality milk to a baby.

The disclosures shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the examples described above may be modified within the scope of the appended claims.

What is claimed is:

1. A method for breast milk collection and storage, comprising:
providing a milk container operable to hold and store breast milk for an extended period of time, the milk container comprising:
a container wall comprising an oxygen blocking layer, a light blocking layer, and an inner surface that is non-adherent for lipids, proteins, and other hydrophobic moieties;
a container opening surrounded by the container wall; and
a foil seal operable to seal the container opening, wherein an internal volume of the milk container has 4% or less of oxygen prior to being filled with breast milk;
piercing the foil seal with a flapper valve, wherein the flapper valve comprises a lower lip operable to prevent the flapper valve from inverting when piercing the foil seal; and
filling the milk container with breast milk,
wherein the internal volume of the milk container has 10% or less of oxygen after being filled with the breast milk;
wherein the breast milk experiences a less than 10% increase in the concentration of lipid peroxides, photodegradation, and/or lipid adsorption during the extended period of time,
wherein the extended period of time is up to 12 days.

2. The method of claim 1 further comprising storing the milk container at 2-8° C.

3. The method of claim 2, wherein the breast milk has a composition that is suckled quality such that it is at least 60-100% identical in enzymatic content and at least 90-100% identical in lipid and lipid peroxide content to milk provided to baby directly from the breast in real time.

4. The method of claim 1 further comprising attaching a flange body adapter having a first end and a second end to a breast pump flange at the first end and the milk container at the second end.

5. The method of claim 1, wherein the milk container further comprises a cooling element docking area, and wherein the method further comprises:
docking the cooling element docking area of the milk container on at least one quick cooling element of a quick cooling apparatus; and
cooling the breast milk in the milk container using the quick cooling apparatus.

* * * * *

UNITED STATES PATENT AND TRADEMARK OFFICE
CERTIFICATE OF CORRECTION

| | | |
|---|---|---|
| PATENT NO. | : 11,975,127 B2 | Page 1 of 1 |
| APPLICATION NO. | : 17/018955 | |
| DATED | : May 7, 2024 | |
| INVENTOR(S) | : Colin Marafko | |

It is certified that error appears in the above-identified patent and that said Letters Patent is hereby corrected as shown below:

On the Title Page

Item (71), APPLICANT:
"Lactation Biocience LLC" should be -- Lactation Bioscience LLC --

Signed and Sealed this
Twenty-seventh Day of August, 2024

Katherine Kelly Vidal
*Director of the United States Patent and Trademark Office*